United States Patent [19]

Warne

[11] Patent Number: 4,746,514
[45] Date of Patent: May 24, 1988

[54] HYDROGEL MATERIALS FORMED BY RADIATION POLYMERIZATION OF CARBOHYDRATES AND UNSATURATED MONOMERS

[75] Inventor: Kevin J. Warne, Swindon, England

[73] Assignee: The Secretary of State for Defence in Her Britannic Majesty's Government of the United Kingdom of Great Britain and Northern Ireland, London, England

[21] Appl. No.: 775,003

[22] Filed: Sep. 11, 1985

[30] Foreign Application Priority Data

Sep. 11, 1984 [GB] United Kingdom ............... 8422950

[51] Int. Cl.⁴ .................... A61F 13/00; C08F 2/54
[52] U.S. Cl. .................................. 424/445; 522/64; 522/69; 527/313; 527/314
[58] Field of Search ............... 527/201, 202, 313, 314; 204/157.63, 157.68; 424/445; 522/64, 69

[56] References Cited

U.S. PATENT DOCUMENTS

| | | | |
|---|---|---|---|
| 3,296,109 | 1/1967 | Leavitt | 204/157.63 |
| 3,600,122 | 8/1971 | Coleman | 527/201 |
| 4,193,845 | 3/1980 | Kaetsu et al. | 527/201 |
| 4,349,470 | 9/1982 | Battista | 527/201 |
| 4,451,629 | 5/1984 | Tonaka et al. | 527/313 |
| 4,541,871 | 9/1985 | Obayashi et al. | 527/314 |
| 4,587,319 | 5/1986 | Towinier | 527/314 |

FOREIGN PATENT DOCUMENTS

| | | | |
|---|---|---|---|
| 2612846 | 7/1976 | Fed. Rep. of Germany | 527/314 |
| 1490128 | 10/1977 | United Kingdom | 527/314 |

OTHER PUBLICATIONS

Walsh et al., Textile Research Journal, Jul. 1965, pp. 648–654.

*Primary Examiner*—Joseph L. Schofer
*Assistant Examiner*—Peter F. Kulkosky
*Attorney, Agent, or Firm*—William R. Hinds

[57] ABSTRACT

Homogeneous hydrogels comprise a water-soluble sugar, derivative or mixture thereof, radiation cross-linked with at least one ethylenically unsaturated compound. A preferred combination is sucrose or glucose cross-linked with acrylic acid. The hydrogels may contain additives e.g. plasticizers such as glycerol. The hydrogels are strong and expand to a large extent e.g. 30× on water absorption. They are particularly suitable for use in medical dressings, preferably bonded to a supporting film which may be a semi-permeable membrane allowing control of water loss. A method for preparing such a hydrogel and dressing is also described.

31 Claims, No Drawings

HYDROGEL MATERIALS FORMED BY RADIATION POLYMERIZATION OF CARBOHYDRATES AND UNSATURATED MONOMERS

This invention relates to hydrogel materials, and has particular but not necessarily exclusive reference to ionising radiation induced formation of uniformly dispersed reactive radicles on molecules of biological origin such as sugars and sugar derivatives.

Hydrogels are polymeric materials which have the ability to imbibe a large fraction of their own weight of water, the absorption being accompanied by swelling. They are frequently used in areas of medicine because of their associated biocompatability, this partly being due to the high water content and tissue-like consistency. Uses are mainly in the fields of wound dressings and implantations into the body in the form of various devices.

A considerable disadvantage of previous types of material is the extreme loss in strength associated with high water content. This often necessitates bonding to a supporting material to aid durability, relying on surface adhesion or chemical bonding for attachment. An adhesive quality is also useful in attaching the gel to the skin, for example in a wound dressing application or for bonding to other high water content surfaces, but this is largely lacking in known hydrogels.

Present hydrogel materials are made from cross-linked monomers in solution or by radiation grafting polymeric films. Common monomers used include methacrylic acid, acrylic acid, hydroxyethyl methacrylate, ethyl methacrylate, vinyl pyrrolidone, acrylamide, as well as various esters and imides, which monomers have the characteristic of containing a reactive group such as a vinyl group. Polymerisation can be achieved by using heat or high energy radiation, the most common method being to cure by thermal methods in the presence of initiators. This often necessitates initiator removal after polymerisation because of the undesirability of most such compounds in the final product. The gels posess varying degrees of hydrophilicity depending on the monomers used and the method of polymerisation but none combine the desirable properties of a high water uptake, high degree of surface adhesion, biocompatibility and strength.

According to the present invention there is provided an homogeneous hydrogel material comprising a water-soluble organic material, selected from the group consisting of monosaccharides, disaccharides, trisaccharides, tetrasaccharides and pentasaccharides and derivatives thereof, radiation crosslinked in aqueous solution with at least one water-soluble ethylenically unsaturated compound having at least one hydrophilic group appendant thereto.

Monosaccharides may be pentoses, hexoses or heptoses, but hexoses, being either pyronose or furonose are preferred. Disaccharides are preferably dihexoses, but other combinations of hexose, heptose, pentose and tetrose saccharide systems may be used. Naturally occurring sugars are preferred as a class as these are easily obtainable in a pure form.

Preferred monosaccharides are glucose and fructose, but other aldohexoses, and deoxy pentoses may used. Preferred disaccharides are sucrose, maltose and lactose, but other hexosidotetroses, pentosidohexoses, hexosidopentoses, deoxyhexosidohexoses, hexosidohexoses (glucosidoglucoses, galacto-sidoglucoses, glucosidomannoses, galactosidogalactoses and galacto-sidomannoses, and glycosidofructoses), and hexasidohexoses (glucosidoaldosides, glucosidoketosides) may be used.

Derivatives of sugars may include alkyl or alkoxyl substituted sugars, esters with organic, eg carboxylic, acids, inorganic acids, halides, acid derivatives eg sugar acids such as tetrahydroxy mono carboxylic acids, trihydroxyaldehydrocarboxylic acids, trihydroxydicarboxylic acids, pentahydroxymonocarboxylic acids, dehydroxyhexonic acids, uronic acids, tetrahydroxy dicarboxylic acids and the corresponding disaccharide equivalents, amino derivatives such as glycamines, acetals, ketals, hemiacetals, glycosides, aldehyde and ketone derivatives, and allyl ethers.

Sugars and sugar derivatives may be mixed in any proportion in the hydrogels of the invention.

The crosslinking compound should be an ethylenically urated compound, ie containing at least one $C=C$ (ethylenic) unit. The substituents on the ethylenic unit include at least one group which is or contains a hydrophilic group, such as hydroxyl (OH), carboxylic acid ($CO_2H$) or amide ($CONH_2$) which are preferred, but other hydrophilic groups may also be used such as soluble ketones or aldehydes, lower amines or sulphonates.

The crosslinking compound should preferably be soluble in water or aqueous media.

Vinyl compounds are preferred, eg acrylic acid and its salt, eg Na, K, Ca or $NH_4$, salts, acrylonitrile, acrylamide, and substituents, eg cyano- or alkyl substitutents such as methyl and ethyl substituents thereof. Vinyl pyrrolidone and substituted forms of vinyl pyrrolidone may also be used. Acrylic acid is most preferred as its use results in hydrogels which are generally tacky, biocompatible and highly expansile on contact with water.

Polymers of these cross-linking compounds may also be used in the hydrogels of the present invention provided that the polymer contains one or more ethylenic units.

The relative proportions of the sugar, derivative or mixture, and the cross-linking compound are variable between broad limits best determined experimentally with the aim of achieving physical strength, water-swelling characteristics and other properties suitable for an intended application.

The proportion of the sugar or derivative in the hydrogel should be greater than that which results in a crystalline polymer and should be sufficient that the hydrogel is homogeneous. An excess of the sugar or derivative may result in a structure in which not all is cross-linked. It is necessary that substantially all the sugar or derivative is cross-linked in the structure.

A proportion of the cross-linking compounds in excess of that necessary to cross-link all of the sugar or derivative may be used, as the excess cross-linking compound may be used up in polymerising with itself. As the proportion of the cross-linking compound is increased however the hydrogel tends to become stronger, more rubbery, but less water-swellable.

Generally a weight percentage of at least 20% of the sugar, derivative or mixture should be present in the hydrogel.

Additives may also be incorporated in the hydrogel of the present invention to modify the properties of the hydrogel. For example plasticizers may be included, one preferred form of plasticizer being water-soluble long chain saturated or unsaturated alcohols and polyols such as glycerol, sorbitol, octanol and higher alkanols.

The hydrogels of the invention may be made by a method comprising the steps of (a) selecting a water-soluble organic material from the group consisting of monosaccharides, disaccharides, trisaccharides, tetrasaccharides, and pentasaccharides and derivatives thereof;

(b) selecting at least one water-soluble ethylenically unsaturated compound having at least one hydrophilic group appendant thereto;

(c) forming a mixture in aqueous solution of the selected products of steps (a) and (b), the solution containing at least 20% by weight of the water-soluble material; and (d) exposing the aqueous solution to ionising radiation until an homogeneous hydrogel material is formed.

The sugar, sugar derivative, unsaturated compounds and additives if used may be any of the compounds discussed above. The aqueous solution may be made up in water, or in a mixture of water and a water-miscible inert solvent eg an alcohol such as ethanol or methanol or a ketone such as acetone to encourage dissolution of the reactants. It is desirable to use as high a proportion of water as possible in the solvent if pure water is not used. The reactants are mixed in solution in the proportions in which they are to be present in the final hydrogel. It is desirable to use a highly concentrated solution of the reactants which may be viscous syrups or pastes. No upper concentration limit other than that requird to produce a solution of manageable viscosity appears to exist. On cross-linking, the solution sets in situ into a hydrogel and the physical strength of this gel will depend to a large extent on the amount of water which is incorporated into its structure, the more incorporated water, the weaker will be the hydrogel until ultimately gelling does not occur. As the hydrogel is normally intended to swell in use by absorption of water, the degree of water swelling will also be determined by the amount of incorporated water present in the hydrogel, a large initial water content resulting in a lower degree of water-swelling on subsequent wetting.

Preferred limits of water content in the hydrogel are 20–90 wt %. The lower limit is determined by the solubility of the reactants, usually the cross-linking compound and the upper limit being the limit for gelling to occur.

The preferred mole ratio of the organic material to the at least one ethylenically unsaturated compound in the product and method of the present invention is from 1:1 to 1:20.

For the hydrogels and the method of the present invention it is essential that the cross-linking reaction be carried out by exposing the solution of reactants to radiation. Radiation cross-linking enables the advantage of cross-linking of sugars and derivatives thereof which do not contain reactive groups.

A preferred type of radiation is gamma radiation for example from a Co 60 source. A suitable dose of gamma radiation is 0.1M rads to 10M rads, and a preferred dose rate is from 0.0005 to 3.0M rads/hr. Other forms of ionising radiation eg short wave ultraviolet radiation, bombardment with electrons from a linear accelerator or x-rays may also be used at an appropriate total dose and dose rate. The degree of cross linkage increases with an increase in the total radiation dose, and for a given dose, increases with a decrease in dose rate.

The cross-linking reaction may be carried out at room temperatures or at temperatures up to 100° C. It is preferable to remove dissolved gases from the reaction mixture to prevent the inclusion of bubbles in the hydrogel. It is also desirable to perform the reaction in the absence of an $O_2$-containing atmosphere as reactive oxidising species may otherwise be formed.

On completion of the cross-linking reaction the solution will have set into a hydrogel of generally the same shape as the original solution if contained in a vessel. The subsequent treatment of the hydrogel will depend upon the intended application, and may include washing, drying to remove unwanted water (eg air-drying at a slightly elevated temperature, max 50° C.), or if medical applications are intended, re-sterilising eg with radiation.

Additives such as plasticizers, eg glycerol, may be incorporated in the hydrogel by including them in the reaction mixture prior to cross-linking. Alternatively such additives may be incorporated by soaking the hydrogel in a medium, preferably an aqueous medium containing the additive. Incorporation by diffusion then occurs. A hydrogel into which additives have been incorporated may then be dried and sterilized as above.

The hydrogels of the present invention may be produced in a physically strong form by the method of the invention. Their most important characteristic though is their ability to absorb a large amount of water in addition to any water which they may contain initially, this absorbtion being accompanied by swelling, in some cases up to tens of times their original volume. The hydrogels of the invention also retain this absorbed water to a substantial extent, resisting loss by for example evaporation. This water absorbancy is a consequence of the presence of a large number of water-coordinating hydrophilic sites such as the —OH groups of the sugar molecules incorporated in the hydrogel.

The hydrogels of the invention also have a number of other useful properties. They may be transparent, have gel-like consistency, and have an adhesive surface enabling them to be permanently bonded to a wide range of materials. They have a paticular advantage in that they may be bonded to wet materials or to materials having a high surface water concentration as bond strength increases as the material becomes more hydrated. Any bond involving the hydrogel of the invention, if made after cross-linking, may be delaminated easily by the application of liquid water to the interface and peeling.

These properties of the hydrogels of the invention make them especially suitable for use in medical applications, eg medical dressings. For such medical applications is is of course desirable that the hydrogel and the materials of it is made and which are incprorated in it are bio-compatible and non toxic. The biocompatibility or otherwise of a hydrogel material of the invention may be determined by standard medical toxicity tests. For use in wound dressings, hydrogels containing acrylamide are not recommended.

For use as a medical dressing a hydrogel according to the invention may be used alone but is preferably used bonded to a supporting or reinforcing film or films. The film may be an outer layer and in such a form may preferably be a semi-permeable membrane which enables controlled transport of water from the site of the dressing. The semipermeable membrane may conveniently be one of the graft copolymeric materials described in the Applicants UK Pat. No. 2035350 and copending patent application PCT/GB No. 85/00197. The former patent discloses copolymers comprising a base polymer selected from the group consisting of polyolefins, partially or fully fluorinated polyolefins, polyether urethanes, polymethylsiloxanes, polyethylene glycolterephthalates, polyamides, polyacrylonitriles, polyvinylchlorides, polyvinylidenechlorides, polyvinylalcohols, polyethyleneglycols, polyvinylpyrrolidones and copolymers of the monomers of two or more of the said polymers graft copolymerised with an ethylenic carboxylic acid. The latter application discloses acrylic acid grafted polyethylene—vinyl acetate copolymers.

In a dressing of this type, it is desirable that the semipermeable membrane retains some water within its structure to prevent the hydrogel from drying out but at the same time to prevent excess exudate from building up at the site of the wound. For this reason the membrane preferably is of a material which has a water content in equilibrium with distilled water at 20° C. of from 2 to 13 weight %. Between these limits the membrane will control water loss from the gel and hence from the site of the wound, the minimum water content being that required to prevent exudate buildup and the maximum being that required to prevent the gel from drying out on the wound, since water loss from the membrane will increase with increasing equilibrium water content. This water content may be produced in a copolymer described in PCT/GB85/00197 in the form of a 60 micron thickness film produced by taking a polyethylene vinyl acetate film containing 12.5% vinyl acetate and grafting in 26 wt% acrylic acid. The graft copolymer will adhere slightly to polyethylene when hydrated and has an optimised water and oxygen permeability (equilibrium water content: 10 wt%). It is also strong, durable and impenetrable to bacteria. Reduction of the amount of acrylic acid in the graft copolymer reduces the equilibrium water content.

A dressing may also comprise a composite structure of two or more different hydrogels, for example one based on a sugar or derivative, such as sucrose, and another based on a protein such as gelatin. In general, the protein based hydrogel may be prepared in generally the same manner as the previously mentioned hydrogels of the invention. For this purpose, the proteins may be naturally occurring or synthetic, animal or vegetable derived or may be derived from microbiological culture. They may be polypeptides or shorter polyamino acids. They should preferably be soluble, desirably highly soluble, in water and aqueous media, and should also preferably contain a high proportion, e.g., more than 5% by weight of hydroxyl-containing amino acids such as hydroxyproline, serine, threonine or hydroxylisine. Proteins from animal sources may inclue blood proteins, fibrinogen, and gelatin, being a hydrolyzed collagen. Gelatin is a preferred protein as it contains many polyhydroxyl groups which enhance solubility and can form a common link with sugars and derivatives thereof, and also forms a strong elastic structure at bodily temperatures. The field of available proteins is so large that subject to express limitations discussed herein, no specific class of proteins or protein derivatives is excluded from use in the protein based hydrogel of the composite structure.

In another form of medical dressing using the hydrogels of the invention, a fabric material may be impregnated with the hydrogel, for example by soaking the fabric in the solution prior to exposure to radiation, and a semipermeable membrane may be bonded onto one (the outer) surface. The fabric may be a non-woven, semi-transparent cellulose material, this being sufficiently absorbent to allow easy impregnation, the thickness of the hydrogel layer being determined by the thickness of the fabric. Ideally such a fabric should consist of fibres which are disposed in such a manner as to allow gel expansion in the thickness direction by their separation. The fibrous material should be non-elastic to prevent curling of the composite dressing that would otherwise occur from longitudinal expansion of the hydrogel.

Alternative methods of preparation of dressings using the hydrogels of the invention are to cast the monomer solution on to a non-fibrous transparent matrix or to bond the gel layer to a cover-film after polymerisation.

A dressing made by one of the above methods has the advantage that it will exhibit a controlled adhesion to the skin, obviating the need for a further bandage or adhesive material, but at the same time allowing easy release from sensitive, burn type wounds by the application of water and gentle peeling. The property that gives the dressing this characteristic is the higher affinity of the gel surface for water than for skin. The cover film provides strength, protection from infection, and a controlled rate of water loss due to its graduated hydration with gel/wound wetness. The maximum rate of water loss is limited by the maximum water content of the film which is low compared with that of the gel. The film also allows the dressing to be wrapped completely around an appendage and held under tension using the ability of the gel surface to bond well to the back of the copolymer on the overlapping region. This bond is stronger than the one between gel and skin. The dressing has a very high absorptive capacity and can posess varying degrees of transparency depending on the nature and thickness of the supporting matrix. An alternative cover material may comprise a crosslinked gelatin based gel.

Hydrogels according to the invention may be used for other medical and non-medical purposes. Other used include a fluid absorbing device for example an incontinence—controlling device, either alone or in combination with other materials such as flexible foams or fabrics, or as tissue implants, implanted devices or part thereof, in controlled drug release devices, in permselective membranes, in electrophoresis, in enzyme immobilisation, in contact lenses and any other biomedical application requiring a high degree of biocompatibility or in admixture with media employed in horticulture, in culture media used in bacteriology and in any other applications requiring the present of retained moisture for supporting growth.

The invention will now be described by way of example.

EXAMPLE 1

A 2 ml mixture of (a) 800 grams/liter concentration of sucrose in water with (b) acrylic acid was made, the volumes being in the ratio 6:4 The monomer solution was irradiated in the absence of gaseous oxygen with gamma radiation from a cobalt 60 source at a dose rate of 0.104 Mrads/Hr for a total dose of 2.5M rads. The product was a sterile gel with all the properties mentioned, having in particular an adhesive surface and an expansile capability in distilled water of around 30 times the original volume.

EXAMPLE 2

A 2 ml mixture of (a) a sucrose solution in water of concentration 800 g/l with (b) an equal volume of acrylic acid was irradiated as described in Example 1. This produced a gel which expanded 7 times its volume on hydration, which was tough and had a slightly tacky surface.

EXAMPLE 3

A mixture of (a) a sucrose solution in water of concentration 800 g/l with the addition of 20% of ethanol was added to (b) an equal volume of acrylic acid and irradiated as described in Example 1. This produced a gel which had a tacky surface and expanded unevenly on hydration to 8 times it volume.

EXAMPLE 4

A mixture of (a) a sucrose solution in water of concentration 800 g/l with (b) an equal volume of acrylamide solution in water of concentration 500 g/l were irradiated as described in Example 1. This produced a smooth gel which expanded to 4 times its volume on hydration and exhibited a non-tacky surface.

EXAMPLE 5

A mixture of (a) a glucose solution in water of concentration 800 g/l with (b) an equal volume of acrylic acid was irradiated as described in Example 1. This produced a tacky gel which expanded to 5.5 times its volume, with some residual solidified glucose on the under-surface.

EXAMPLE 6

A mixture of (a) sucrose solution in water of concentration 800 g/l with an (b) equal volume of vinyl pyrrolidone was irradiated as described in Example 1. The product was a soft fluid-like gel on hydration.

EXAMPLE 7

A gel was produced as described in Example 1 but using a radiation dose rate of 0.047M rads/hr to a total dose of 0.8M rads. This produced a gel of similar properties to that produced in Example 1, but with an expansile capability in distilled water of around 60 times the original volume.

EXAMPLE 8

Glycerol was incorporated into the hydrogel of Example 1 as follows. A prepared hydrogel sample (2 g) was placed in distilled water (1 L). It was left for 24 hr to swell the hydrogel. The water was then replaced with fresh filtered and double distilled water (1 L), and a magnetic stirrer was used to agitate the water for 3 hr. The replacement of water and period of stirring was repeated twice, then the sample was then placed in a 25 wt% solution of glycerol in water for 8 hr, then removed, surface washed with distilled water and then dried in a 50° C. oven for 24 hours, resting on a low density polyethylene support. The sample was placed in an airtight container and sterilised with gamma radiation using 2.5M rads at a dose rate of 0.5M rads hr$^{-1}$.

EXAMPLE 9

A medical dressing was made by cutting both a hydrated sheet of a 26 wt% acrylic acid-polyethylene vinyl acetate graft copolymer as described above and a fibrous cellulose material to be a close fit to the internal dimensions of a polythylene envelope of the required dressing size so that a gap of 1 cm was left at the open end. The two layers were then placed, copolymer face down, in the envelope. The copolymer sheet was firmly pressed to the inside of the envelope by the application of light pressure and smoothed to remove wrinkles. The open end of the envelope was then heat sealed adjacent to the 2 layers, leaving an open gap of 2 cm at one corner. An excess of the monomer solution, prepared as in Example 1, was poured into the unsealed corner and allowed to drain down to the bottom. A roller was used to control the even application of the solution to the two layers, firstly expelling air bubbles and then expelling the surplus solution to give an even impregnation. The aperture at the end of the envelope was then dried and heat sealed. The whole was then placed between two glass plates and clamped lightly to flatten the sample and prevent inward oxygen diffusion. This was then irradiated, the dose and dose rate being as specified in Example 1. The resulting dressing was sterile and prepackaged. In use it was easily removed from the envelope by cutting and peeling from the polyethylene.

EXAMPLE 10

A gelatin-based film suitable for forming a cover for a hydrogel of the invention for use in a medical dressing was made by mixing a heated gelatin solution containing 260 grams/liter of gelatin in water at 50 degrees Celsius with acrylic acid in a volume ratio of 6:1. The gel was cured in a gaseous oxygen free environment using gamma radiation at a dose rate of 0.6M rads/hr to a total dose of 3M rads. The gel was bonded to a sucrose gel layer by adhesion. The gelatin gel had a tough, elastic rubbery consistency and conferred strength, conformability and elasticity to the dressing.

Partial dehydration of the opaque white gelatin gel gives a transparent brown material with little loss in elasticity.

EXAMPLE 11

A standard cytotoxicity elution test using MRC-5 human ebryonic lung fibroblasts was carried out on each of three hydrogel samples prepared in accordance with the above Examples. Results were as follows:

| Sample 1 (Example 8) | 1+ at zero dilution<br>0 at 1 in 2 dilution<br>pH = 3.1<br>nominally toxic |
|---|---|
| Sample 2 (Example 8) | below scoring level<br>pH = 3.3<br>not toxic |
| Sample 3 (Example 1) | 1+ at zero dilution<br>0 at 1 in 2 dilution<br>pH = 3.0<br>nominally toxic |

Negative control = tissue culture fluid
Positive control = Medical grade latex (result 4+ highly toxic)

These tests demonstrate that medical grade latex is around 100 times more toxic than the hydrogel samples. They also demonstrate that the addition of glycerol or other aliphatic polyols is preferred since they tend to reduce the cytotoxicity of the resulting hydrogels which are then more suitable for use in biomedical applications such as wound dressings.

I claim:

1. An homogeneous hydrogel material comprising a water-soluble organic material, selected from the group consisting of monosaccharides, disaccharides, trisaccharides, tetrasaccharides, and pentasaccharides and derivatives thereof, radiation crosslinked in aqueous solution with at least one water-soluble ethylenically unsaturated compound having at least one hydrophilic group appendant thereto.

2. A medical dressing containing a hydrogel material according to claim 1 wherein the at least one ethylenically unsaturated compound comprises an ethylenically unsaturated carboxylic acid.

3. A medical dressing according to claim 2 wherein the ethylenically unsaturated carboxylic acid comprises acrylic acid.

4. A hydrogel material according to claim 1 wherein the organic material is selected from the group consisting of monosaccharides, disaccharides, and derivatives thereof.

5. A hydrogel material according to claim 2 wherein the organic material is selected from sucrose and derivatives thereof.

6. A hydrogel material according to claim 1 wherein the at least one ethylenically unsaturated compound is selected from ethylenically unsaturated carboxylic acids and derivatives thereof.

7. A hydrogel material according to claim 5 wherein the ethylenically unsaturated carboxylic acid is acrylic acid.

8. A hydrogel material according to claim 5 wherein the derivative of the ethylenically unsaturated carboxylic acid comprises acrylamide.

9. A hydrogel material according to claim 1 wherein the at least one ethylenically unsaturated compound comprises vinyl pyrrolidone.

10. A hydrogel material according to claim 1 wherein the mole ratio of the organic material to the at least one ethylenically unsaturated compound in the hydrogel is from 1:1 to 1:20.

11. A hydrogel material according to claim 1 wherein the hydrogel contains in addition a plasticiser.

12. A hydrogel material according to claim 10 wherein the plasticiser comprises an aliphatic polyol.

13. A hydrogel material according to claim 11 wherein the polyol is glycerol.

14. A medical dressing according to claim 2 comprising a composite structure including a layer of said hydrogel material and a further layer including a hydrogel material based on a protein or protein derivative.

15. A medical dressing according to claim 14 wherein the hydrogels are based on sucrose and gelatin respectively.

16. A medical dressing according to claim 2 comprising a layer of the hydrogel material bonded to a supporting or reinforcing backing film.

17. A medical dressing according to claim 16 wherein the backing film is a semi-permeable membrane.

18. A medical dressing according to claim 17 wherein the membrane is a hydrophilic thermoplastic graft copolymer.

19. A medical dressing according to claim 18 wherein the copolymer is a base polymer selected from the group consisting of polyolefins, partially or fully fluorinated polyolefins, polyetherurethanes, polydimethylsiloxanes, polyethylene glycolterephthalates, polyamides, polyacrylonitriles, polyvinylchlorides, polyvinylidenechlorides, polyvinylalcohols, polyethyleneglycols, polyvinylpyrrolidones and copolymers of the monomers of two or more of said polymers graft copolymerised with an ethylenic carboxylic acid.

20. A medical dressing according to claim 18 wherein the copolymer is an acrylic acid grafted polyethylene—vinyl acetate copolymer.

21. A medical dressing according to claim 17 wherein the copolymer has an equilibrium water content at 20° C. of 2 to 13% by weight.

22. A medical dressing according to claim 2 wherein the hydrogel material is impregnated into a fabric material.

23. A medical dressing according to claim 22 wherein the fabric material is a non-woven cellulose material.

24. A method of preparing a hydrogen material which comprises the steps of
 (a) selecting a water-soluble organic material from the group consisting of monosaccharides, disaccharides, trisaccharides, tetrasaccharides, and pentasaccharides and derivatives thereof;
 (b) selecting at least one water-soluble ethylenically unsaturated compound having at least one hydrophilic group appendant thereto;
 (c) forming a mixture in aqueous solution of the selected products of steps (a) and (b), the solution containing at least 20% by weight of the water-soluble organic material; and
 (d) exposing the aqueous solution to ionising radiation until an homogeneous hydrogel material is formed.

25. A process according to claim 24 wherein the organic material is selected from the group consisting of monosaccharides, disaccharides, derivatives of monosaccharides, and derivatives of disaccharides.

26. A method according to claim 24 comprising the further step of
 (e) replacing at least part of the aqueous solution content of the product of step (d) with an aliphatic polyol.

27. A method according to claim 24 wherein the ionising radiation is gamma radiation.

28. A method according to claim 26 wherein the total dose of gamma radiation administered in step (d) is from 0.1M rads to 10 M rads.

29. A method according to claim 26 wherein the radiation dose rate in step (d) is from 0.0005 to 3M rads/hr.

30. A method according to claim 24 wherein the aqueous solution formed in step (c) contains from 20% to 90% water.

31. A method according to claim 24 wherein the mole ratio of the organic material to the at least one ethylenically unsaturated compound in the aqueous solution formed in step (c) is from 1:1 to 1:20.

* * * * *